US012611328B2

(12) United States Patent
Kuebler et al.

(10) Patent No.: US 12,611,328 B2
(45) Date of Patent: Apr. 28, 2026

(54) OPHTHALMOSURGICAL APPLIANCE

(71) Applicant: Carl Zeiss Meditec AG, Jena (DE)

(72) Inventors: Christoph Kuebler, Oberkochen (DE);
Susanne Kohlhammer, Blaustein (DE);
Markus Neumaier, Aalen (DE)

(73) Assignee: Carl Zeiss Meditec AG, Jena (DE)

( * ) Notice: Subject to any disclaimer, the term of this
patent is extended or adjusted under 35
U.S.C. 154(b) by 1036 days.

(21) Appl. No.: 17/732,494

(22) Filed: Apr. 28, 2022

(65) Prior Publication Data

US 2022/0249283 A1 Aug. 11, 2022

Related U.S. Application Data

(63) Continuation of application No.
PCT/EP2020/080248, filed on Oct. 28, 2020.

(30) Foreign Application Priority Data

Oct. 29, 2019 (DE) ..................... 10 2019 216 669.5

(51) Int. Cl.
*A61F 9/007* (2006.01)

(52) U.S. Cl.
CPC ................................. *A61F 9/00745* (2013.01)

(58) Field of Classification Search
CPC ........ A61M 2210/0612; A61F 9/00781; A61F
9/00736; A61F 9/007; A61F 9/00745
See application file for complete search history.

(56) References Cited

U.S. PATENT DOCUMENTS 5,676,650 A * 10/1997 Grieshaber ............. A61M 1/77
417/205
7,303,566 B2 * 12/2007 Kishimoto .......... A61F 9/00736
604/27

(Continued)

FOREIGN PATENT DOCUMENTS

CN 101969896 A 2/2011
CN 102665621 A 9/2012

(Continued)

OTHER PUBLICATIONS

International Search Report dated Feb. 4, 2021 of international
application PCT/EP2020/080248 on which this application is based.

(Continued)

*Primary Examiner* — Scott J Medway
(74) *Attorney, Agent, or Firm* — Ewers IP Law PLLC;
Falk Ewers

(57) ABSTRACT

An ophthalmosurgical appliance includes an irrigation fluid
line through which irrigation fluid can flow from an irriga-
tion fluid container to an ophthalmosurgical handpiece for
phacoemulsification, a first fluid pump configured to convey
the irrigation fluid to the handpiece, a first volumetric flow
determination device configured to determine a first volu-
metric flow, an aspiration fluid line, a second fluid pump
configured to convey aspiration fluid to the collecting con-
tainer, a second volumetric flow determination device con-
figured to determine a second volumetric flow, a difference
element configured to form a difference from the first
volumetric flow and the second volumetric flow to form a
differential volumetric flow signal, and a control device
configured to determine, from the differential volumetric
flow signal and the irrigation fluid setpoint pressure signal,
a signal for an irrigation fluid control pressure to supply this (Continued)

signal at an output of the control device to the first fluid pump.

9 Claims, 2 Drawing Sheets

(56) References Cited

U.S. PATENT DOCUMENTS

| | | | |
|---|---|---|---|
| 8,894,605 | B2 | 11/2014 | Eichler |
| 11,510,811 | B2 | 11/2022 | Boukhny et al. |
| 2002/0019607 | A1 | 2/2002 | Bui |
| 2005/0209561 | A1 | 9/2005 | Gordon et al. |
| 2006/0224107 | A1 | 10/2006 | Claus et al. |
| 2012/0232466 | A1 | 9/2012 | Kuebler et al. |
| 2012/0302941 | A1 | 11/2012 | Teodorescu et al. |
| 2013/0237900 | A1 * | 9/2013 | Hauger ................... A61M 1/77 604/22 |
| 2014/0114236 | A1 * | 4/2014 | Gordon .............. A61F 9/00745 604/28 |
| 2016/0220751 | A1 * | 8/2016 | Mallough ............... A61M 1/72 |
| 2018/0318131 | A1 | 11/2018 | Boukhny et al. |
| 2019/0099529 | A1 | 4/2019 | Mehta et al. |
| 2019/0099547 | A1 | 4/2019 | Mehta et al. |
| 2021/0290836 | A1 | 9/2021 | Koeppel |

FOREIGN PATENT DOCUMENTS

| | | | | |
|---|---|---|---|---|
| CN | 103561662 | A | 2/2014 | |
| CN | 104640523 | A | 5/2015 | |
| CN | 104661624 | A | 5/2015 | |
| CN | 109952119 | A | 6/2019 | |
| DE | 102015003799 | A1 | 9/2016 | |
| DE | 102017215677 | B3 | 11/2018 | |
| EP | 1765190 | A2 | 3/2007 | |
| WO | 2005092022 | A2 | 10/2005 | |
| WO | 2005092023 | A2 | 10/2005 | |
| WO | WO-2008030872 | A1 * | 3/2008 | .............. A61M 1/74 |
| WO | 2016150754 | A1 | 9/2016 | |
| WO | WO-2019020150 | A1 * | 1/2019 | ........ A61F 9/00745 |
| WO | 2019236615 | A1 | 12/2019 | |
| WO | 2020033736 | A1 | 2/2020 | |

OTHER PUBLICATIONS

International Preliminary Report on Patentability of the European Patent Office in PCT/EP2020/080248 (from which this application claims priority) mailed May 12, 2022 and English translation thereof.

Office Action issued in German Patent Application No. DE 10 2019 216 669.5, dated Oct. 12, 2020 (from which this application claims priority) and English language translation thereof.

Office Action dated Nov. 22, 2022 issued in Japanese counterpart application No. 2022-523581 and English-language translation thereof.

Office Action and Search Report dated Nov. 18, 2022 issued in Chinese counterpart application No. 202080076000.3 and English-language translation thereof.

U.S. Appl. No. 17/732,501, filed Apr. 28, 2022, Christoph Kuebler.

* cited by examiner

OPHTHALMOSURGICAL APPLIANCE

CROSS REFERENCE TO RELATED APPLICATIONS

This application is a continuation application of international patent application PCT/EP2020/080248, filed Oct. 28, 2020, designating the United States and claiming priority to German application 10 2019 216 669.5, filed Oct. 29, 2019, and the entire content of both applications is incorporated herein by reference.

TECHNICAL FIELD

The disclosure relates to an ophthalmosurgical appliance.

BACKGROUND

There are a number of surgical techniques for treating clouding of the crystalline lens, which is referred to in medicine as cataract. The most widespread technique is phacoemulsification, in which a thin hollow needle (phaco needle) is inserted by a handpiece into the crystalline lens and is induced to vibrate by ultrasound. In the process, an irrigation fluid is supplied. In its immediate environment, the vibrating hollow needle emulsifies the crystalline lens in such a way that the resulting lens particles can be aspirated through the hollow needle, and through a line connected thereto and referred to as an aspiration line, with an aspiration pump. When the crystalline lens has been completely emulsified and removed, a new artificial lens can be inserted into the empty capsular bag, and so a patient treated in this way can recover good vision.

The technique of phacoemulsification has been a relatively safe one. However, it has been observed that, during phacoemulsification, the intraocular pressure often fluctuates to a very large extent, which can be dangerous for a patient. If the intraocular pressure drops sharply, the cornea moves within a short time in the direction of the iris, as a result of which the convex surface of the cornea changes, becoming uneven, partially concave and undulating. This adversely affects the surgeon's view during the operation, and it therefore becomes unclear to the surgeon where the tip of a phaco needle is located at such a moment. There is therefore an increased risk of the phaco needle accidentally piercing a posterior wall of the capsular bag. This causes the patient serious damage, of the kind that does not heal by itself or that may not be healed by medical interventions.

With the technique available today, there are a number of safety mechanisms that seek to avoid a strong fluctuation of intraocular pressure. However, it has been reported that, despite such safety mechanisms, such fluctuations of the intraocular pressure occur even in situations that are supposedly not dangerous.

SUMMARY

It is an object of the disclosure to make available an ophthalmosurgical appliance which, with minimal complexity, allows phacoemulsification to be performed with little fluctuation or no significant fluctuation of the intraocular pressure.

The object is achieved by the subject matter of the independent claim 1. Advantageous developments of the disclosure are the subject matter of the dependent claims.

The ophthalmosurgical appliance according to the disclosure has:

an irrigation fluid line through which irrigation fluid can flow from an irrigation fluid container to an ophthalmosurgical handpiece for phacoemulsification, a first fluid pump which is arranged, in the direction of flow, between the irrigation fluid container and the handpiece and which is configured to convey irrigation fluid to the handpiece, a first volumetric flow determination device which is arranged, in the direction of flow, between the first fluid pump and the handpiece and which is configured to determine a first volumetric flow, an aspiration fluid line through which aspiration fluid can flow from the handpiece to a collecting container, a second fluid pump which is arranged, in the direction of flow, between the handpiece and the collecting container and which is configured to convey aspiration fluid to the collecting container, a second volumetric flow determination device which is arranged, in the direction of flow, between the handpiece and the second fluid pump and which is configured to determine a second volumetric flow, a difference element which is coupled to the first volumetric flow determination device and to the second volumetric flow determination device and which is configured to form a difference from the first volumetric flow and the second volumetric flow, in order to form a differential volumetric flow signal, a control device with a first input for receiving the differential volumetric flow signal and a second input for receiving a signal for an irrigation fluid setpoint pressure, wherein the control device is configured to determine, from the differential volumetric flow signal and the irrigation fluid setpoint pressure signal, a signal for an irrigation fluid control pressure and to supply this signal at an output of the control device for the first fluid pump.

The disclosure is based on the knowledge that a fluctuation of intraocular pressure can occur not only when an occlusion at the tip of a phaco needle arises, resulting in a relatively high underpressure very quickly normalizing in the aspiration line. A fluctuation of intraocular pressure can also occur when there is no occlusion at the phaco needle, i.e. when lens particles and fluid are aspirated entirely normally and without any disturbance of the operation. The inventors have observed that irrigation fluid can always escape at the site where the phaco needle punctures the cornea. Such a puncture site is larger than the diameter of a phaco needle since, prior to the insertion of the phaco needle, another surgical instrument was used to perform capsulorhexis, which requires a larger opening than the phaco needle. When the phaco needle is subsequently inserted through this opening, an escape of irrigation fluid at this opening is unavoidable during phacoemulsification. Such loss of irrigation fluid occurs in an irregular manner, since a surgeon, while performing phacoemulsification, moves the phaco needle to and fro and irregularly in the puncture site. During the phacoemulsification, the surgeon takes care to ensure that the hard crystalline lens is successfully crushed. However, he cannot ensure that only a small or a uniform amount of irrigation fluid escapes through the puncture site, so as to avoid a fluctuation of the intraocular pressure.

This problem is solved by the ophthalmosurgical appliance according to the disclosure. A leak at the puncture site in the eye being treated, hence the loss of irrigation fluid, can be detected by comparing a first volumetric flow in the irrigation fluid line with a second volumetric flow in the aspiration line. To this end, a first volumetric flow determination device is provided which is arranged, in the direction of flow, between the first fluid pump and the handpiece and which is configured to determine a first volumetric flow. Moreover, a second volumetric flow determination device is provided which is arranged, in the direction of flow, between the handpiece and the second fluid pump and which is configured to determine a second volumetric flow, A difference element, which is coupled to the first volumetric flow determination device and to the second volumetric flow determination device, is configured to form a difference from the first volumetric flow and the second volumetric flow, in order to form a differential volumetric flow signal.

If the difference from the first volumetric flow and the second volumetric flow is zero, there is no leak at the puncture site in the eye. However, if the difference is larger than zero, there is a leak at the opening through which the phaco needle penetrates the cornea. According to an aspect of the disclosure, this differential volumetric flow signal can be supplied to a first input of a control device, which is configured to receive, at a second input, a signal for an irrigation fluid setpoint pressure. The control device processes the differential volumetric flow signal and the signal for the irrigation fluid setpoint pressure in such a way that a signal for an irrigation fluid control pressure is made available at an output of the control device, in order to supply said signal to the first fluid pump. The pressure of the irrigation fluid in the irrigation fluid line is then changed by the first fluid pump such that the loss of irrigation fluid at the opening in the cornea can be compensated, as a result of which a fluctuation of the intraocular pressure proves to be minimal or does not occur at all. There is little complexity in the use of a first volumetric flow determination device and a second volumetric flow determination device and in the processing of a derived difference signal and in the corresponding actuation of the first fluid pump. Since the normal operation without occlusion at the phaco needle accounts for a large part of the time taken up during the phacoemulsification, a fluctuation of the intraocular pressure during this time can be kept minimal or avoided with the appliance according to the disclosure, and this represents a considerable improvement compared to conventional appliances for phacoemulsification.

The control device typically has a multiplication element which is configured to receive the differential volumetric flow signal at an input and to output a signal for a differential pressure at an output. The multiplication element thus converts the differential volumetric flow signal to a pressure signal. Furthermore, the control device has an addition element which is configured to receive a signal for the irrigation fluid setpoint pressure at a first input and to receive the signal for the differential pressure at a second input and, at an output, to supply a signal for the irrigation fluid control pressure to the output of the control device. The addition element thus processes two pressure values and adds them. The signal for the irrigation setpoint pressure can be supplied from an input device, for example a foot pedal. The sum of the two pressures can then be supplied as control pressure to the first fluid pump in the irrigation fluid line.

According to an exemplary embodiment, the ophthalmosurgical appliance has a first timing element which is configured to predefine the profile of the irrigation fluid setpoint pressure as a function of time, wherein the first timing element is coupled to the second input of the control device. The quantity of an irrigation fluid setpoint pressure does not therefore have to be supplied abruptly by use of an on/off switch of the control device, and instead, on account of the first timing element, can increase slowly, for example according to an exponential function or a higher-order function, to the quantity of the irrigation fluid setpoint pressure. In this way, it is possible to avoid excessively quick pressure changes in the irrigation fluid line, which would propagate in the irrigation fluid line as far as the handpiece and the eye and could cause instability of the eye.

A first time constant of the first timing element is typically adjustable. Depending on the type of first fluid pump, the length of the irrigation fluid line, the cross section of the irrigation fluid line and the nature of the inner wall of the irrigation fluid line, it is possible on the one hand to achieve a rapid change of the pressure in the irrigation fluid line with the adjustable time constant of the first timing element. If the time constant is adjustable, it is possible, on the other hand, for a switching-on process and a switching-off process to be controlled such that overshooting of a signal is avoided. It is thereby possible to obtain an end value not through a step function, but instead with a time delay, despite which this still takes place quickly. This is advantageous from the medical point of view, since an eye is therefore not exposed to sudden stresses during an operation, and therefore geometric movements of the eye take place in an attenuated manner.

According to a further exemplary embodiment, a second timing element is provided which is configured to predefine the profile of the aspiration fluid setpoint pressure as a function of time and supply it to the second fluid pump. A second time constant of the second timing element is particularly typically adjustable. Thus, the setpoint pressure in the aspiration line can slowly increase, for example according to an exponential function or a higher-order function, to the quantity of the aspiration fluid setpoint pressure. This has the effect that no additional pressure fluctuations are introduced into the aspiration line simply through actuation of the second fluid pump. Particularly typically, the ophthalmosurgical appliance has both the first timing element and the second timing element, the respective time constants of which are adjustable. Thus, depending on the length and nature of the irrigation fluid line as far as the handpiece, and of the aspiration line, it is possible for the increase of a setpoint pressure in the irrigation fluid line and in the aspiration line to be adjusted such that, during the phacoemulsification, the intraocular pressure remains almost or completely constant while the amount of irrigation fluid lost through a leak at the cornea changes.

The first time constant can lie in a range of 50 milliseconds to 1000 milliseconds, and the second time constant can lie in a range of 50 milliseconds to 1000 milliseconds. An almost stable or completely stable intraocular pressure can be achieved in a particularly reliable manner if a difference between the first time constant and the second time constant has a quantity that lies in a range of larger than zero and less than 200 milliseconds.

BRIEF DESCRIPTION OF THE DRAWINGS

The disclosure will now be described with reference to the drawings wherein.

DESCRIPTION OF EXEMPLARY EMBODIMENTS

Figure 1:
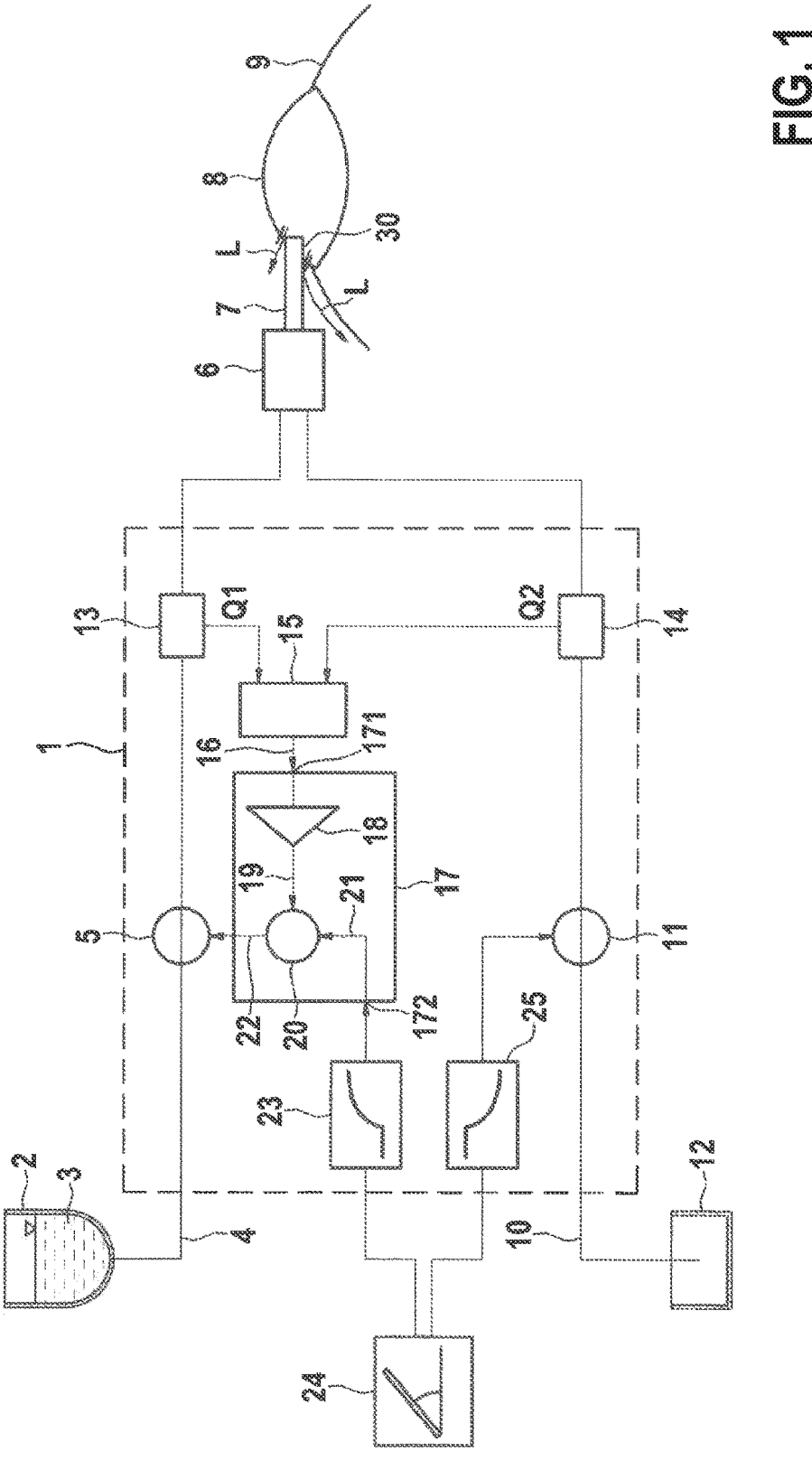
FIG. 1 shows an ophthalmosurgical appliance according to an exemplary embodiment of the disclosure.

FIG. 1 shows a schematic view of an ophthalmosurgical appliance 1 according to an exemplary embodiment of the disclosure. An irrigation fluid container 2 contains an irrigation fluid 3 which, through an irrigation fluid line 4 connected to the container, is guided to a first fluid pump 5, which can be a diaphragm pump. From there, the irrigation fluid 3 can flow along the irrigation fluid line 4 as far as a handpiece 6 for the phacoemulsification, and pass through a phaco needle 7, which is inserted through a cornea 8, to a crystalline lens of an eye 9 that is to be treated. During operation of a second fluid pump 11, which is a suction pump such as a diaphragm pump for example, emulsified lens particles and fluid can pass through a line inside the phaco needle 7 and inside the handpiece 6 and along an aspiration fluid line 10 to the second fluid pump 11. From the second fluid pump 11, the lens particles and the fluid, i.e., the aspiration fluid as a whole, are conveyed along the aspiration fluid line 10 to a collecting container 12.

A first volumetric flow determination device 13 with which a first volumetric flow Q1 in the irrigation fluid line 4 can be determined is arranged, in the direction of flow, between the first fluid pump 5 and the handpiece 6. The first volumetric flow Q1 is typically determined indirectly by the volumetric flow determination device 13, for example by a position of a diaphragm or of a float being detected and the volumetric flow being determined therefrom. A second volumetric flow determination device 14 with which a second volumetric flow Q2 in the aspiration line 10 can be determined is arranged, in the direction of flow, between the handpiece 6 and the second fluid pump 11. The signal of the first volumetric flow Q1 and the signal of the second volumetric flow Q2 are passed to a difference element 15 which is configured to form a difference from the first volumetric flow Q1 and the second volumetric flow Q2, in order to form a signal 16 in accordance with a differential volumetric flow DQ. The signal 16 is therefore the difference from Q1 minus Q2.

This signal 16 is supplied to a first input 171 of a control device 17 and passes there to a multiplication element 18 which is configured to receive the signal 16 at an input and to output a signal 19 for a differential pressure at an output. The control device 17 moreover has an addition element 20 which is configured to receive a signal 21 for the irrigation fluid setpoint pressure at a first input and to receive the signal 19 for the differential pressure at a second input. The addition element 20 processes these two signals 19 and 21 in such a way that the sum thereof is formed in order, at an output of the addition element 20, to supply a signal 22 for an irrigation fluid control pressure to the output of the control device 17. The signal 22 for the irrigation fluid control pressure is then supplied to the first fluid pump 5, which accordingly changes the pressure of the irrigation fluid 3 in the irrigation fluid line 4.

If the difference from the first volumetric flow and the second volumetric flow is zero, the signal 22 for the irrigation fluid control pressure is likewise zero, and the first fluid pump 5 experiences no change in terms of its actuation. However, if the signal 16 is not equal to zero and usually larger than zero, the first fluid pump 5 experiences, through the signal 22, a change in terms of its actuation, such that it changes the pressure for the irrigation fluid 3 in the irrigation fluid line 4. This therefore counteracts the unwanted discharge of fluid from the eye 9 caused by a leak 30 (see arrow labeled L in FIG. 1).

The ophthalmosurgical appliance 1 additionally has a first timing element 23 which is configured to predefine the profile of the irrigation fluid setpoint pressure as a function of time. The first timing element 23 is coupled to a second input 172 of the control device 17, whereupon the signal 21 for the irrigation fluid setpoint pressure is supplied to the addition element 20. The first timing element 23 is coupled to a foot pedal 24 which, when suitably actuated by an operator, obtains a signal for the irrigation fluid setpoint pressure.

The foot pedal 24 is additionally coupled to a second timing element 25 to which, upon associated actuation of the foot pedal 24, a signal for an aspiration fluid setpoint pressure can be supplied. The second timing element 25 is configured to predefine the profile of the aspiration fluid setpoint pressure as a function of time, which profile can then be supplied to the second fluid pump 19.

Figure 2:
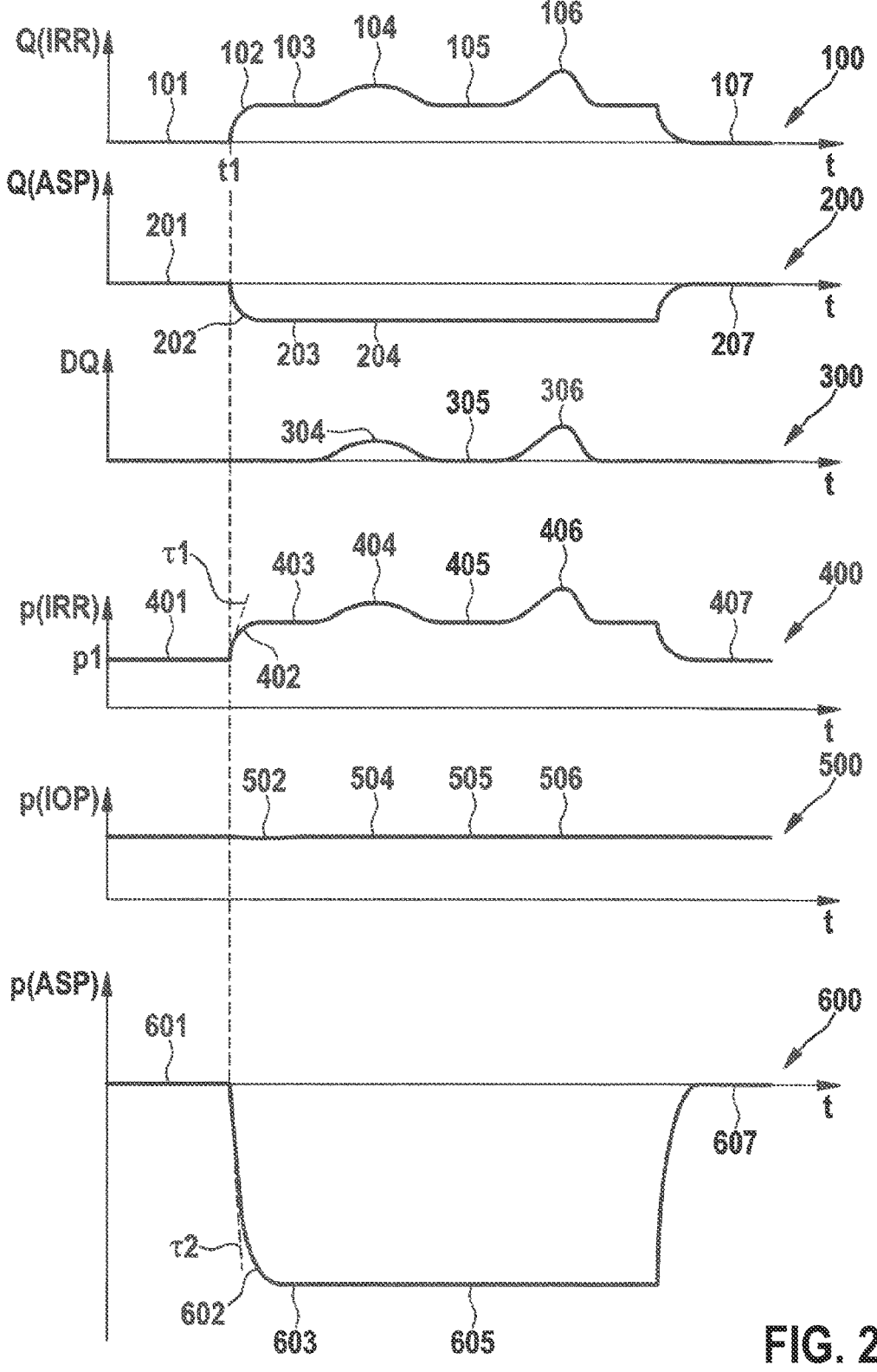
FIG. 2 shows schematic diagrams of volumetric flow profiles and pressure profiles as a function of time during use of the ophthalmosurgical appliance.

FIG. 2 shows a number of schematic diagrams of volumetric flow profiles and pressure profiles as a function of time.

Diagram 100 shows a profile of an irrigation fluid volumetric flow Q(IRR) as a function of time. In the time period to the time t1, there is still no irrigation fluid flowing through the irrigation fluid line (see 101 in diagram 100). This also applies to the aspiration fluid in the aspiration fluid line; see 201 in diagram 200, which shows the profile of the aspiration fluid volumetric flow Q(ASP) as a function of time. In the irrigation fluid line, there is a stationary pressure p1 up to the time t1; see 401 in diagram 400, which shows the profile of the irrigation fluid pressure p(IRR) as a function of time. In the aspiration fluid line, the aspiration pressure is equal to zero up to the time t1; see 601 in diagram 600, which shows the aspiration fluid pressure p(ASP) as a function of time. The intraocular pressure p(IOP) is shown as a function of time in diagram 500. It will be seen from this that up to the time t1 the intraocular pressure is larger than zero, which corresponds to the normal state of the eye.

It is assumed that at the time t1 the foot pedal is actuated, such that the first fluid pump 5 and the second fluid pump 11 each pump fluid. The irrigation fluid volumetric flow increases (see 102) and reaches a stationary value (see 103 in diagram 100). At the same time, the aspiration fluid volumetric flow also increases (see 202) and likewise reaches a stationary value (see 203 in diagram 200). Since irrigation fluid flows in the irrigation fluid line and aspiration fluid flows in the aspiration line, an associated fluid pressure also builds up in these lines. The irrigation fluid pressure p(IRR) increases (see 402) and reaches a stationary value (see 403 in diagram 400). In the same way, the aspiration fluid pressure increases (see 602) and reaches a stationary value (see 603 in diagram 600). If the first time constant τ1 for the increase of the irrigation fluid pressure and the second time constant τ2 for the increase of the aspiration fluid pressure differ by not more than 200 milliseconds, there is only a slight fall or no fall at all in the intraocular pressure (see 502 in diagram 500).

If a loss of irrigation fluid now occurs because a leak 30 is present at the eye, the irrigation fluid pressure drops in the irrigation fluid line 4 between the first pump 5 and the phaco needle 7, such that the first pump 5 provides a larger irrigation fluid volumetric flow (see 104). The aspiration fluid volumetric flow is unaffected by this and remains constant (see 204). With the ophthalmosurgical appliance 1 according to the disclosure, a difference between the irrigation fluid volumetric flow and the aspiration fluid volumetric flow is determined that is larger than zero (see 304 in diagram 300, which shows a differential volumetric flow DQ as a function of time). A signal of the irrigation fluid setpoint pressure and a signal of a differential pressure are thus received from the addition element 20, such that a correspondingly increased irrigation fluid control pressure acts on the first fluid pump 5 (see 404). While irrigation fluid escapes from a leak 30 at the eye 9, there is therefore a higher irrigation fluid pressure in the irrigation fluid line. The consequence of this is that, during this time, the intraocular pressure in the eye remains unchanged (see 504).

When the extent of the leak 30 decreases again, for example as a result of a different position of the phaco needle, and therefore an unwanted discharge of irrigation fluid at the eye also decreases, the first fluid pump can maintain the usual irrigation fluid pressure with a smaller volumetric flow (see 105). The differential volumetric flow thus reduces (see 305). The irrigation fluid pressure thus again reaches the setpoint pressure (see 405) which corresponds to the pressure according to 403. The intraocular pressure remains unchanged (see 505). The pressure in the aspiration fluid line is unaffected by this (see 605).

The fluctuation of the irrigation fluid volumetric flow may also be relatively high (see 106), as a result of which a larger value for the differential volumetric flow DQ is detected (see 306). This leads to a larger change of the irrigation fluid pressure (see 406), such that the intraocular pressure can remain unchanged (see 506).

When the foot pedal is no longer actuated, the first pump 5 and the second pump 11 are not activated, and therefore the irrigation fluid volumetric flow and the aspiration volumetric flow drop to the zero value (see 107 and 207). The pressures in the irrigation fluid line and in the aspiration line then also drop (see 407 and 607).

It is understood that the foregoing description is that of the exemplary embodiments of the disclosure and that various changes and modifications may be made thereto without departing from the spirit and scope of the disclosure as defined in the appended claims.

LIST OF REFERENCE NUMERALS

1 Ophthalmosurgical appliance
2 Irrigation fluid container
3 Irrigation fluid
4 Irrigation fluid line
5 First fluid pump
6 Ophthalmosurgical handpiece
7 Phaco needle
8 Cornea
9 Eye
10 Aspiration fluid line
11 Second pump
12 Collecting container
13 First volumetric flow determination device
14 Second volumetric flow determination device
15 Difference element
16 Differential volumetric flow signal
17 Control device
18 Multiplication element
19 Differential pressure signal
20 Addition element
21 Irrigation fluid setpoint pressure signal
22 Irrigation fluid control pressure signal
23 First timing element
24 Foot pedal
25 Second timing element
171 First input of the control device
172 Second input of the control device
DQ Differential volumetric flow
L Leak
p Pressure
p(ASP) Aspiration fluid pressure
p(IOP) Intraocular pressure p(IRR) Irrigation fluid pressure
Q1 First volumetric flow
Q2 Second volumetric flow
Q(ASP) Aspiration fluid volumetric flow
Q(IRR) Irrigation fluid volumetric flow
t Time
τ Time constant

What is claimed is:

1. An ophthalmosurgical appliance, comprising:
an irrigation fluid line, arranged between an irrigation fluid container and an ophthalmosurgical handpiece for phacoemulsification, through which irrigation fluid can flow from the irrigation fluid container to the ophthalmosurgical handpiece, wherein the irrigation fluid container and the ophthalmosurgical handpiece are connected to the ophthalmosurgical appliance;
a first fluid pump arranged, in a first direction of flow, between the irrigation fluid container and the ophthalmosurgical handpiece and configured to convey the irrigation fluid to the ophthalmosurgical handpiece;
a first volumetric flow meter arranged, in the first direction of flow, between the first fluid pump and the ophthalmosurgical handpiece and configured to determine a first volumetric flow rate;
an aspiration fluid line, arranged between the ophthalmosurgical handpiece and a collecting container connected to the ophthalmosurgical appliance, through which aspiration fluid can flow from the ophthalmosurgical handpiece to the collecting container;
a second fluid pump arranged, in a second direction of flow, between the ophthalmosurgical handpiece and the collecting container and configured to convey the aspiration fluid to the collecting container;
a second volumetric flow meter arranged, in a second direction of flow, between the ophthalmosurgical handpiece and the second fluid pump and configured to determine a second volumetric flow rate;
a differential flow meter coupled to the first volumetric flow determination device meter and to the second volumetric flow meter and configured to determine a difference between the first volumetric flow rate and the second volumetric flow rate and to output a differential volumetric flow rate signal; and
a first controller with a first input configured to:
receive the differential volumetric flow rate signal as a first input and a signal for an irrigation fluid setpoint pressure as a second input,
generate, from the differential volumetric flow rate signal and an irrigation fluid setpoint pressure signal, a signal for an irrigation fluid control pressure, and
supply the signal for the irrigation fluid control pressure to the first fluid pump.

2. The ophthalmosurgical appliance as claimed in claim 1, wherein the first controller includes an adder,
wherein the adder has a first input, a second input, and an output,
wherein the first controller is further configured to:
receive the differential volumetric flow rate signal,
generate a signal for a differential pressure,
provide the signal for the irrigation fluid setpoint pressure to the first input of the adder,
provide the signal for the differential pressure to the second input of the adder, and,
supply the signal for the irrigation fluid control pressure from the output of the adder to an output of the first controller.

3. The ophthalmosurgical appliance as claimed in claim 1, further comprising:

a foot pedal; and second controller in communication with the foot pedal, coupled to the second input of the first controller, and configured to predefine a profile of the irrigation fluid setpoint pressure as a function of time depending on a degree of actuation of the foot pedal.

4. The ophthalmosurgical appliance as claimed in claim 3, further comprising a third controller in communication with the foot pedal, configured to predefine an aspiration fluid setpoint pressure as a function of time depending on a degree of actuation of the foot pedal and to supply the predefined aspiration fluid setpoint pressure to the second fluid pump.

5. The ophthalmosurgical appliance as claimed in claim 3, wherein the second controller has a first time constant, and wherein the first time constant is adjustable.

6. The ophthalmosurgical appliance as claimed in claim 5, wherein the first time constant lies in a range of 50 milliseconds to 1000 milliseconds.

7. The ophthalmosurgical appliance as claimed in claim 4, wherein the third controller has a second time constant, and wherein the second time constant is adjustable.

8. The ophthalmosurgical appliance as claimed in claim 7, wherein the second time constant lies in a range of 50 milliseconds to 1000 milliseconds.

9. The ophthalmosurgical appliance as claimed in claim 7, wherein a difference between the first time constant and the second time constant has a quantity that lies in a range of larger than zero and less than 200 milliseconds.

* * * * *